United States Patent [19]

Hassler

[11] Patent Number: 4,915,114

[45] Date of Patent: Apr. 10, 1990

[54] SHOCK WAVE SOURCE HAVING CENTRAL LOCATING SYSTEM & DISPOSED IN A CAVITY FREE OF SHOCK WAVES

[75] Inventor: Dietrich Hassler, Uttenreuth, Fed. Rep. of Germany

[73] Assignee: Siemens Aktiengesellschaft, Berlin and Munich, Fed. Rep. of Germany

[21] Appl. No.: 250,846

[22] Filed: Sep. 29, 1988

[30] Foreign Application Priority Data

Oct. 19, 1987 [DE] Fed. Rep. of Germany ....... 3735345

[51] Int. Cl.$^4$ .......................... A61B 8/00; A61B 17/22
[52] U.S. Cl. .............. 128/660.03; 128/24 A; 367/150; 350/412
[58] Field of Search ............... 128/660.03, 24 A, 328; 181/176; 367/150; 350/412; 310/335

[56] References Cited

U.S. PATENT DOCUMENTS

| | | | |
|---|---|---|---|
| 4,001,766 | 1/1977 | Hurwitz . | |
| 4,617,931 | 10/1986 | Dory | 128/328 |
| 4,771,787 | 9/1988 | Wurster et al. | 128/328 |
| 4,776,342 | 10/1988 | Zimmer | 128/660.03 |
| 4,834,106 | 5/1989 | Hassler et al. | 128/328 |
| 4,844,081 | 7/1989 | Northeved et al. | 128/660.03 |

FOREIGN PATENT DOCUMENTS

| | | | |
|---|---|---|---|
| 3617032 | 1/1987 | Fed. Rep. of Germany | 128/328 |
| 3736733 | 5/1988 | Fed. Rep. of Germany | 128/328 |

*Primary Examiner*—Ruth S. Smith
*Attorney, Agent, or Firm*—Hill, Van Santen, Steadman & Simpson

[57] ABSTRACT

A shock wave source for disintegrating a calculus has a centrally disposed cavity in which a locating system for identifying the position of the calculus is disposed. The shock wave source has an emission surface, from which shock waves are emitted into a coupling agent in the shock wave source. The emission surface is angled in the direction of shock wave propagation, so that the shock waves emitted therefrom diverge. A focusing element is provided which focuses the shock waves onto the calculus, the focusing element having a structure which, in addition to focusing the shock waves, compensates for the divergence of the shock waves. Due to the divergence of the shock waves, the central cavity in which the locating system is disposed is maintained free of shock waves.

14 Claims, 2 Drawing Sheets

SHOCK WAVE SOURCE HAVING CENTRAL LOCATING SYSTEM & DISPOSED IN A CAVITY FREE OF SHOCK WAVES

BACKGROUND OF THE INVENTION

1. Field of the Invention

The present invention is directed to a shock wave source for lithotripsy treatment of a calculus, and particularly to such a shock wave source having a means for focusing the shock waves to the calculus, and a locating system for identifying the position of the calculus.

2. Description of the Prior Art & Related Application

A lithotripter having a cavity therein in which a locating system is disposed, which is free of shock waves, is described in European Application 0 148 653. In this shock wave source, a plurality, for example 300 to 400 discrete piezoelectric elements are arranged in a mosaic at the inside surface of a sphere. A recess is provided in the center of the spherical surface, and the head of an ultrasound locating system, with an associated imaging device, is disposed therein. It is a disadvantage of this arrangement, however, that the head of the ultrasound locating system must necessarily be disposed a relatively large distance from the calculus to be observed. The calculus will therefore occupy only a very small area in the overall image.

A shock wave source is described in copending application Ser. No. 210,334, filed in the United States on June 23, 1988 (Reichenberger et al), and assigned to the same assignee as the present application, having a central opening with an ultrasound head of an ultrasound transmission and reception device introduced therein. The opening extends through the coil and membrane, which generate the shock waves upon the application of a high voltage pulse to the coil. This requires additional clamping means be provided for the membrane around this central opening.

SUMMARY OF THE INVENTION

It is an object of the present invention to provide a shock wave source having a central cavity therein in which a locating system is disposed wherein the cavity is maintained free of shock waves without the necessity of additional clamping structure.

It is a further object of the present invention to provide such a shock wave source wherein the head of the locating system disposed in the cavity can be placed relatively close to the patient.

The above objects are achieved in accordance with the principles of the present invention in a shock wave source having an emission face which is outwardly angled in the direction of propagation of the shock waves, and which has a focusing means which, in addition to focusing the shock waves onto the calculus, compensates for the divergence of the shock waves caused by the angled emission surface. By angling the emission surface outwardly, the central cavity in which the locating system is disposed is maintained free of shock waves.

In a preferred embodiment, the emission surface is shaped as the surface of a cone. As used herein, the term "outwardly angled" means that the tip of the angle projects toward the end of the shock wave source from which the shock waves exit to the patient.

In one embodiment of the invention, a planar coil and membrane are used, and an acoustically divergent lens is disposed following the membrane in a direction of shock wave propagation, so that the emission surface is the surface of the lens.

In another embodiment, the coil and membrane themselves are angled to form a conical surface, so that the exposed surface of the membrane forms the emission surface. This embodiment exhibits particularly low losses of acoustic energy.

In all embodiments, the shock wave source is preferably a shock wave source operating in the known electromagnetic manner.

DESCRIPTION OF THE PREFERRED EMBODIMENTS

Figure 1:
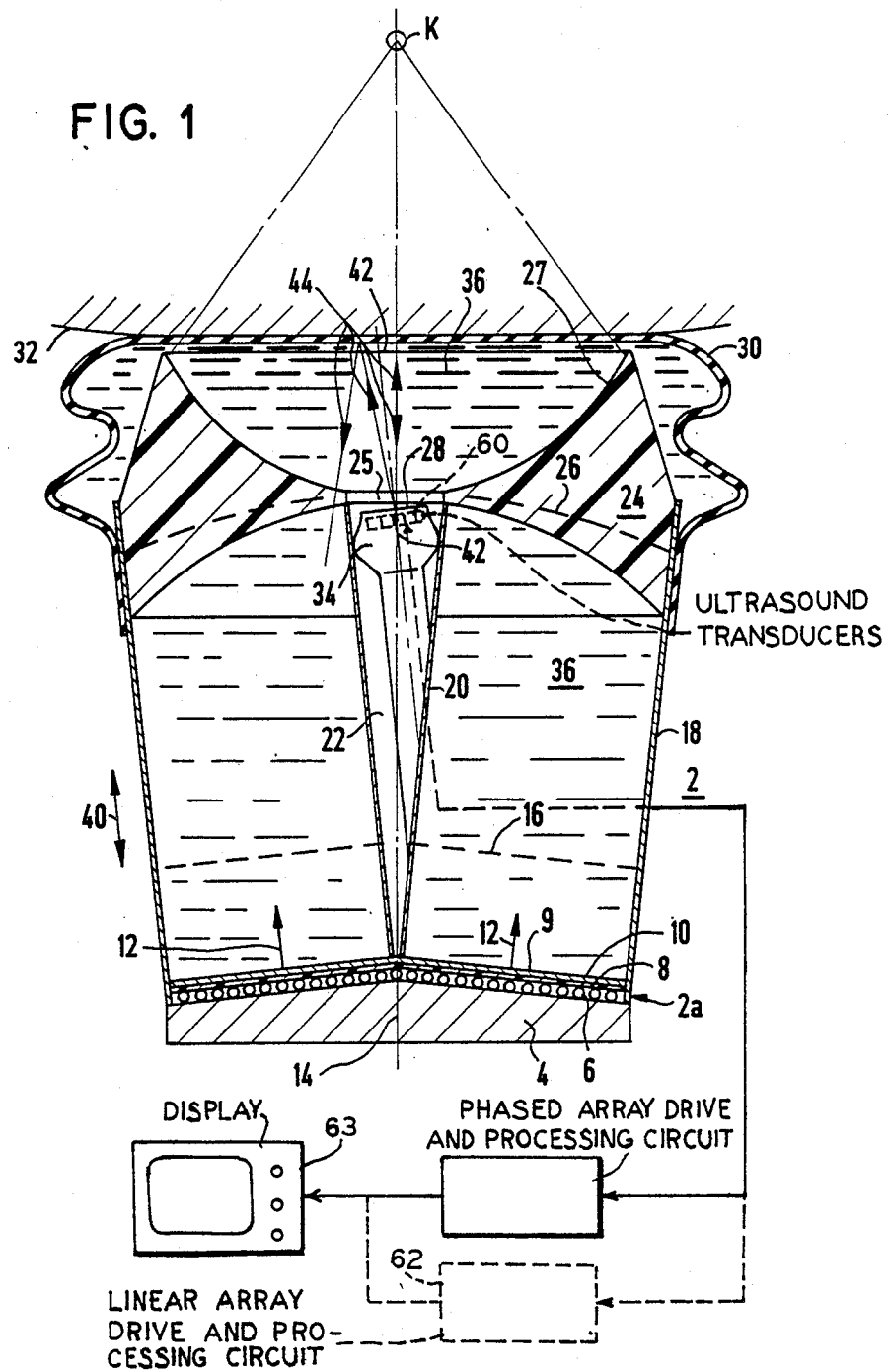
FIG. 1 is a side sectional view of a first embodiment of a shock wave source constructed in accordance with the principles of the present invention.

A shock wave generator 2 is shown in FIG. 1 which operates based on the known electromagnetic principle. The shock wave generator 2 includes a shock wave source 2a, consisting of a circular carrier 4 having a helical coil 6 attached thereto, an insulating foil 8, and an electrically conductive membrane 10. The outer perimeter of the membrane 10 is fastened to the housing of the shock wave generator. The outer or exposed surface of the membrane 10 forms an emission surface 9 of the shock wave source 2a. The coil carrier 4 has a conical shape at the side thereof adjacent the coil 6, so that the coil 6, the insulating foil 8 and the membrane 10 also assume the same conical shape. The emission surface 9 is thus outwardly angled in the emission or propagation direction of the acoustic pulses, indicated by the two arrows 12. As a result, the propagation direction of the acoustic pulses is not parallel to a central axis 14 of the shock wave generator 2; the emission directions 12 each forming an angle relative to the central axis 14 which differs from zero.

The emitted acoustic pulses thus diverge. The divergent propagation of the acoustic pulses is schematically indicated by the dashed line 16, which represents a shock wave front.

The shock wave source 2a is secured at the smaller opening of an expanding conical tube or housing 18. The shock wave source 2a is sealed thereto liquid-tight. The wall of the housing 18 is disposed perpendicularly relative to the surface of the membrane 10, i.e., it is parallel to the emission directions 12 for every cross-section. The shock wave generator 2 has an inside wall 20 which is symmetric relative to the central axis 14, and parallel to the emission direction 12 and the housing 18. The inside wall 20 defines a central cavity 22 which is free of shock waves, and is conical in shape, expanding toward the larger, exit end of the shock wave generator 2.

A focusing element 24 is disposed at the exit end of the housing 18. The focusing element 24 is a biconcave acoustic convergent lens. The focusing element 24 has a central opening 25 in registry with the cavity 22 free of shock waves. The focusing element 24, in addition to performing the conventional function of focusing the shock waves onto a calculus K, also compensates for the divergence of the shock waves due to the angled emission surface 9. For this purpose, the focusing element 24 is thicker than would be the case if the shock waves were propagated with a planar wave front. The dashed line 26 indicates the shape which the focusing elements 24 would have if its only function were to focus the shock waves, the portion 27 functioning for this purpose. By thickening the focusing element 24, the divergence of the shock waves is compensated. The shape of the focusing element 24 is selected according to Snell's Law to avoid spherical aberations.

A coupling sack 30 is attached to the housing 18, sealed liquid-tight, beyond the focusing element 24. The flexible sack 30 permits the shock wave generator 2 to conform to the skin surface 32 of a patient during treatment of the calculus K.

An ultrasound applicator 34, containing ultrasound transmitting/receiving transducers 60, of a locating system is contained in the central cavity 22 to locate and observe the calculus K. The ultrasound applicator 34 has a liquid-tight termination at the base of the inside wall 20. The interior volume of the shock wave generator 2 which is limited by the membrane 10, the housing 18, the inside wall 20 the sack 30 and a portion of the ultrasound applicator 34 is filled with a coupling agent 36, preferably degasified water. Pressure equalization between the two volumes ensues via the opening 25.

The focus of the focusing element 24 is fixed. It can be brought into coincidence with a calculus K in the patient by adjusting the position of the shock wave generator 2 in the direction of the double arrow 40 while maintaining the sack 30 in intimate contact with the skin surface 32. For this purpose, the sack 30 is in the form of a bellows. Further structural details of adjustment means such as, for example, mounts and compensating vessels for the coupling agent 34, are not shown in the drawing.

To avoid multiple reflections between the ultrasound exit face of the ultrasound applicator 34 and the application location at the patient, the exit face of the ultrasound applicator 34 is aligned at an angle relative to the central axis 14. The surface normal 42 of the exit face thus forms an angle relative to the central axis 14 which differs from zero. The path of a reflected ultrasound beam is illustrated by the arrows 44. As shown in the drawing, only the first reflection, which indicates the position of the skin surface 32, is reflected back to the ultrasound applicator 34. Further reflections pass by the applicator 34.

The focusing element 34 consists of material in which the speed of sound is higher tha the speed of sound in water. It is possible to use a focusing acoustic lens wherein the speed of sound is lower than that of water, however, the external contour of the focusing element 24 must then be convex.

The embodiment shown in FIG. 1 has the advantage that no significant structural modifications for the shock wave source 2a of the shock wave generator 2 are necessary to produce a cavity 22 free of shock waves. The shock waves are diverged simply by the conical shape, and significant energy losses are avoided.

Figure 2:
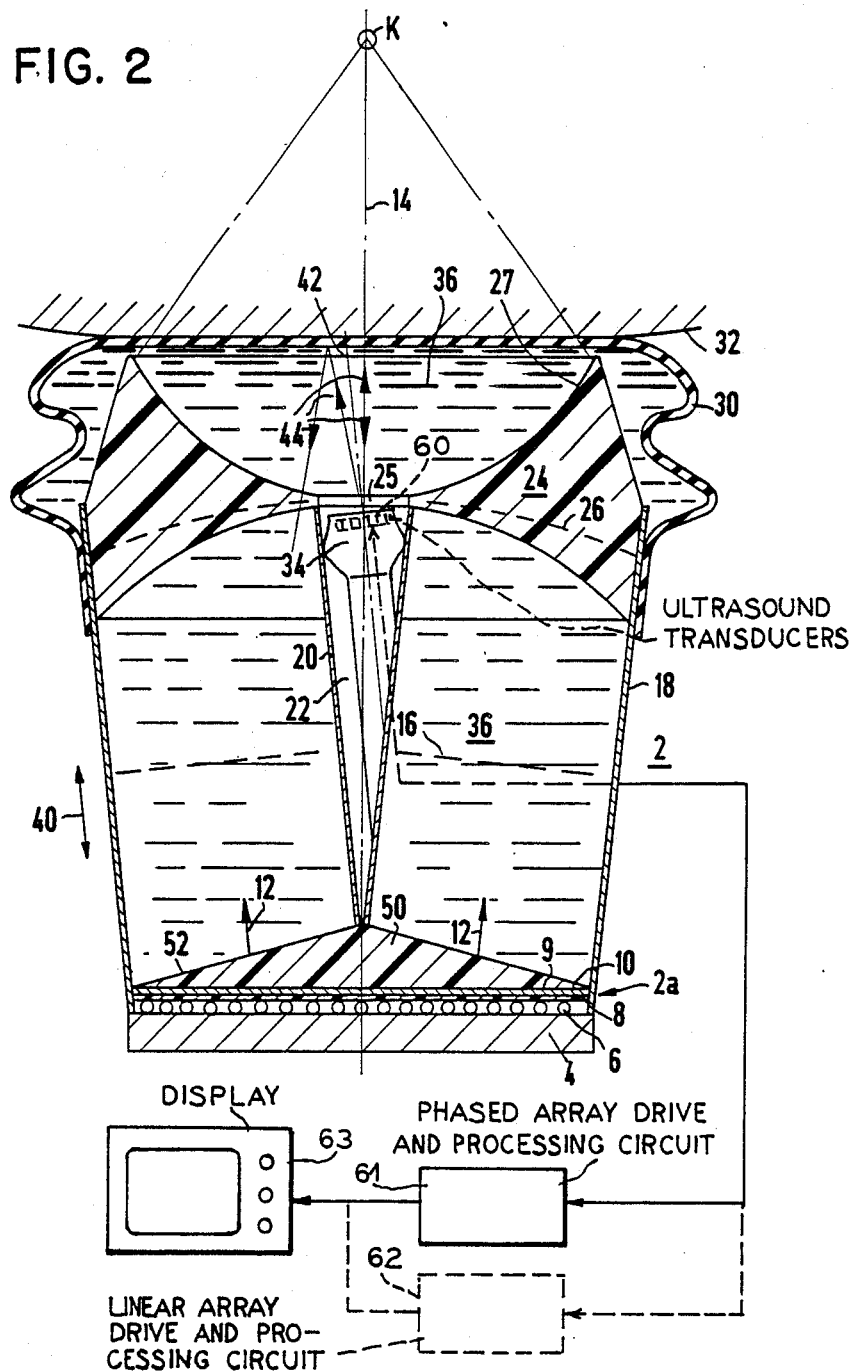
FIG. 2 is a side sectional view of a second embodiment of a shock wave source constructed in accordance with the principles of the present invention.

Another embodiment of a shock wave generator is shown in FIG. 2, wherein components corresponding to those already described in connection with FIG. 1 have the same reference symbols.

The embodiment of FIG. 2 differs from that of FIG. 1 in the construction of the shock wave source 2a. In this embodiment, the coil carrier 4 is a circular disc having a constant thickness. The coil 6 and insulating foil 8 and the membrane 10 are arranged flat on the coil carrier 4. The propagation direction of the acoustic pulses generated by the membrane 10 thus is parallel to the central axis 14. In this embodiment, a divergent acoustic lens 50 is acoustically coupled to the membrane 10. The exposed or outer surface of the lens 50 forms an emission surface 52 in this embodiment. As in the embodiment of FIG. 1, the emission surface 52 is outwardly angled in the emission direction 12. The surface 52 is a conical surface. In this embodiment, however, the emission direction 12 of the acoustic pulses will be at a defined angle relative to the surface 52 dependent upon the speeds of sound in the adjacent media, which can be calculated in a known manner. Unlike the embodiment of FIG. 1, the emission direction 12 thus is not perpendicular to the surface 52.

The remaining structure is the same as in FIG. 1, with the exception that in the embodiment of FIG. 2 the tip of the inside wall 20 is in contact with the tip of the acoustic lens 50, rather than the tip of the membrane 10 (as in FIG. 1).

The advantage of the embodiment of FIG. 2 is that the shock wave source 2a can be constructed in a known planar fashion. It is only necessary to acoustically couple the lens 50 to the membrane 10 to create a central cavity 22 free of shock waves. Although the embodiment of FIG. 2 introduces additional acoustic energy losses, due to the presence of the lens 50, such losses are small enough to be acceptable.

In both of the embodiments of FIGS. 1 and 2, a central cavity 22 free of shock waves is maintained as a result of simple structural measures. It is not necessary in either embodiment to support the membrane 10 by complex retaining structure.

In both embodiments, the ultrasound transducers 60 can be operated either as a phased array, using a phased array drive and processing circuit 61, or as a linear array, using a linear array drive and processing circuit 62. Both circuits 61 and 62 are of known construction. The ultrasound image is reproduced on a display 63.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave generator for lithotripsy treatment of a calculus comprising:
   a housing filled with a shock wave propagating medium;
   a centrally disposed cavity in said housing;
   means disposed in said cavity for locating said calculus;
   means including a shock wave source for emitting shock waves into said medium, said means for emitting having an emission surface disposed in said housing, said emission surface being outwardly angled to diverge said shock waves away from said cavity so that said cavity is free of shock waves; and
   means for focusing said shock waves at said calculus and for compensating for the divergence of said shock waves by said emission surface.

2. A shock wave generator as claimed in claim 1, wherein said emission surface is the surface of a cone.

3. A shock wave generator as claimed in claim 1, wherein said shock wave source has an angled surface, and wherein said emission surface is said surface of said shock wave source.

4. A shock wave generator as claimed in claim 1, wherein said means for emitting shock waves includes a divergent acoustic lens having an angles surface, and wherein said emission surface is said angled surface of said acoustic lens.

5. A shock wave generator as claimed in claim 1, wherein said shock wave source is an electromagnetic shock wave source.

6. A shock wave generator as claimed in claim 1, wherein said means for locating is an ultrasound applicator of an ultrasound locating system.

7. A shock wave generator as claimed in claim 6, wherein said ultrasound locating system includes means for operating an ultrasound array in said ultrasound applicator as an electronic phased array.

8. A shock wave generator as claimed in claim 6, wherein said ultrasound locating system includes means for operating an ultrasound array in said ultrasound applicator as a linear array.

9. A shock wave generator as claimed in claim 1, wherein said means for focusing has a central opening therein in registry with said cavity.

10. A shock wave generator as claimed in claim 1, wherein said means for focusing is a biconcave acoustic convergent lens.

11. A shock wave generator as claimed in claim 1, wherein said housing has an end at which said means for focusing is disposed and which is covered by a flexible sack, and wherein said propagation medium fills a volume between said emission surface and said means for focusing and a volume between said means for focusing and said flexible sack.

12. A shock wave generator for lithotripsy treatment of a calculus comprising:
   a housing filled with a shock wave propagating medium;
   a centrally disposed cavity in said housing;
   means disposed in said cavity for locating said calculus;
   means for emitting shock waves into said propagation medium including, in sequence, an angled carrier, a helical coil disposed on said carrier, an insulating layer, and an elastic electrically conductive membrane, said membrane having a surface in contact with said propagation medium outwardly angled to diverge said shock waves away from said cavity so that said cavity is free of shock waves; and
   means for focusing said shock waves at said calculus and for compensating for the divergence of said shock waves by said outwardly angled surface of said membrane.

13. A shock wave generator as claimed in claim 12, wherein each of said carrier, said coil, said insulating layer and said membrane lie on a surface of a cone.

14. A shock wave generator for lithotripsy treatment of a calculus comprising:
   a housing filled with a shock wave propagating medium;
   a centrally disposed cavity in said housing;
   means disposed in said cavity for locating said calculus;
   means for emitting shock waves into said propagation medium including, in sequence, a planar carrier, a planar coil adjacent said carrier, a planar insulating layer, a planar membrane, and a divergent acoustic lens, said divergent acoustic lens having an outwardly angled surface in contact with said propagation medium to diverge said shock waves away from said cavity so that said cavity is free of shock waves; and
   means for focusing said shock waves at said calculus and for compensating for the divergence of said shock waves by said outwardly angled surface of said divergent acoustic lens.

* * * * *